United States Patent [19]
Frey et al.

[11] Patent Number: 5,541,468
[45] Date of Patent: Jul. 30, 1996

[54] MONOLITHIC TRANSDUCER ARRAY CASE AND METHOD FOR ITS MANUFACTURE

[75] Inventors: Gregg W. Frey, East Wenatchee, Wash.; Jonathan E. Snyder, Whitefish Bay, Wis.

[73] Assignee: General Electric Company, Milwaukee, Wis.

[21] Appl. No.: 343,054

[22] Filed: Nov. 21, 1994

[51] Int. Cl.⁶ ................................................ H01L 41/08
[52] U.S. Cl. ........................................ 310/334; 310/327
[58] Field of Search .................................. 310/326, 327, 310/335, 336, 334, 366

[56] References Cited

U.S. PATENT DOCUMENTS

| | | | |
|---|---|---|---|
| 2,967,956 | 1/1961 | Dranety et al. | 310/327 |
| 3,396,286 | 8/1968 | Anderson et al. | 310/327 |
| 4,446,395 | 5/1984 | Hudjicostis | 310/327 |
| 4,482,834 | 11/1984 | Fleming Dias et al. | 310/327 |
| 4,577,132 | 3/1986 | Ohigashi et al. | 310/800 |
| 4,578,611 | 3/1986 | Sadler | 310/327 |
| 4,680,499 | 7/1987 | Umemura et al. | 310/334 |
| 5,329,682 | 7/1994 | Thurn et al. | 310/334 |
| 5,376,859 | 12/1994 | Kim et al. | 310/334 |
| 5,457,352 | 10/1995 | Muller et al. | 310/327 |

*Primary Examiner*—Thomas M. Dougherty
*Attorney, Agent, or Firm*—Dennis M. Flaherty; John H. Pilarski

[57] ABSTRACT

A monolithic transducer array case having a bottom wall which is suitable for use as an acoustic impedance matching layer in an ultrasonic transducer. The array case is made from electrically conductive material having an acoustic impedance less than the acoustic impedance of piezoelectric ceramic. The preferred material is copper-impregnated graphite.

7 Claims, 4 Drawing Sheets

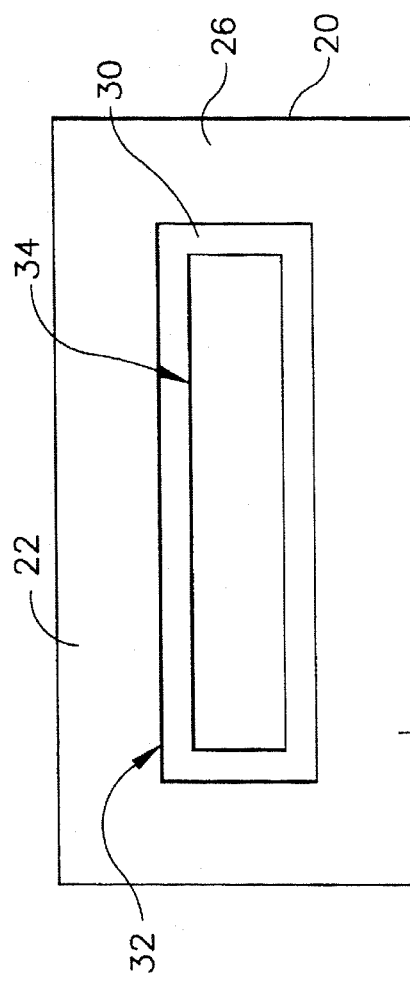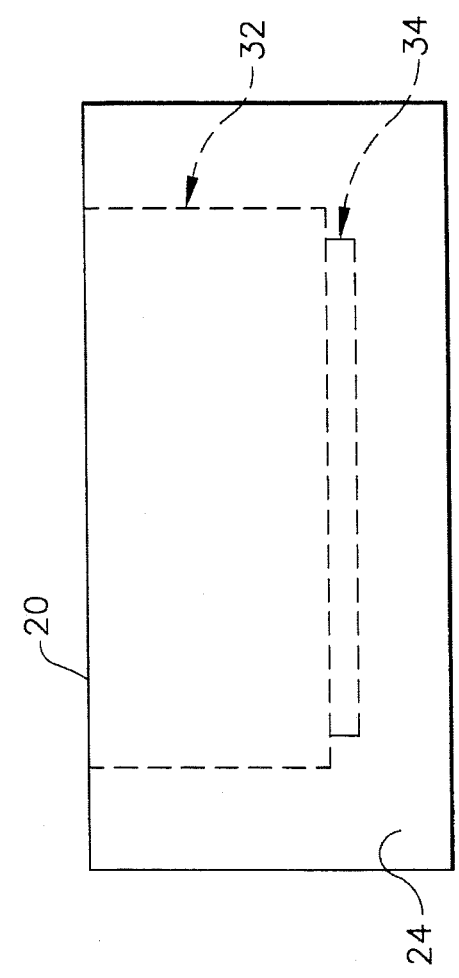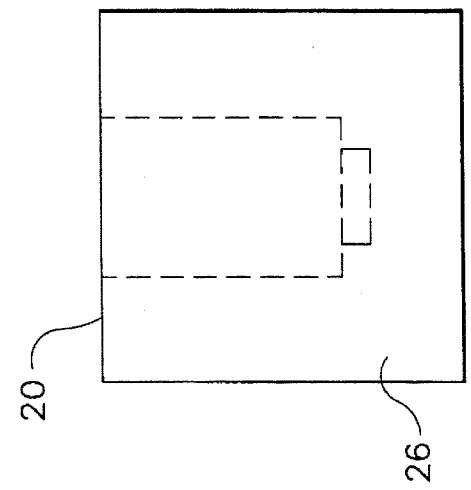

5,541,468

MONOLITHIC TRANSDUCER ARRAY CASE AND METHOD FOR ITS MANUFACTURE

FIELD OF THE INVENTION

This invention generally relates to probes used in ultrasonic imaging of the human anatomy. In particular, the invention relates to ultrasonic transducer arrays for use in electronic beam imagers to make wide-field of view scans.

BACKGROUND OF THE INVENTION

A conventional ultrasonic probe comprises a transducer package which must be supported within the probe housing. As shown in FIG. 1, a conventional transducer package 2 comprises a linear array 4 of narrow transducer elements. Each transducer element is made of piezoelectric ceramic material. The piezoelectric material is typically lead zirconate titanate (PZT), polyvinylidene difluoride, or PZT ceramic/polymer composite.

The design and fabrication of individual transducer elements with desirable acoustic properties, e.g., high sensitivity, wide bandwidth, short impulse response, and wide field of view, is a well known art.

Typically, each transducer element has a metallic coating on opposing front and back faces to serve as electrodes. The metallic coating on the front face serves as the ground electrode. The ground electrodes of the transducer elements are all connected to a common ground. The metallic coating on the back face serves as the signal electrode. The signal electrodes of the transducer elements are connected to respective electrical conductors formed on a flexible printed circuit board (PCB) 6.

One approach for connecting a flexible PCB to a transducer array is a variation of a known high-density interconnect process originally developed for integrated circuit packaging and disclosed in U.S. Pat. No. 5,091,893. Using this technique, a flexible PCB can be fabricated with one end directly connected to a transducer array. To accomplish this, the transducer array is placed in a well formed in a frame with the metallized piezoceramic exposed. An insulating polyimide film is laminated to the surface of the metallized piezoceramic and the surrounding frame, creating a relatively flat surface. A computer-controlled laser then ablates holes in the polyimide layer down to the metal electrode atop the ceramic. A metal layer is applied over the film and follows the hole contour, thereby making electrical contact with the metal electrodes on the ceramic. Conventional photolithographic techniques (25 µm lines and spaces are typical) are used to pattern the metal, thus creating lines from each transducer element to a fanout pattern. Excess polyimide can be removed to provide a good acoustic contact of the backing (described below) to the ceramic element.

Using this method, the resultant flexible PCB can have signal runs which fan out so that the miniature coaxial cables can be attached directly. Since the circuit board is flexible, the wiring assembly can be folded to occupy a very small cross section while retaining considerable freedom for motion.

During operation, the signal and ground electrodes of the piezoelectric transducer elements are connected to an electrical source having an impedance $Z_s$. When a voltage waveform v(t) is developed across the electrodes, the material of the piezoelectric element compresses at a frequency corresponding to that of the applied voltage, thereby emitting an ultrasonic wave into the media to which the piezoelectric element is coupled. Conversely, when an ultrasonic wave impinges on the material of the piezoelectric element, the latter produces a corresponding voltage across its terminals and the associated electrical load component of the electrical source.

In conventional applications, each transducer element produces a burst of ultrasonic energy when energized by a pulsed waveform produced by a transmitter (not shown). The pulses are transmitted to the transducer elements via the flexible PCB 6. This ultrasonic energy is transmitted by the probe into the tissue of the object under study. The ultrasonic energy reflected back to transducer array 4 from the object under study is converted to an electrical signal by each receiving transducer element and applied separately to a receiver (not shown).

Typically, the front surface of each transducer element 4 is covered with one or more acoustic impedance matching layers that improve the coupling with the medium in which the emitted ultrasonic waves will propagate. For the sake of discussion, FIGS. 1 and 2 show a transducer package having two impedance matching layers 8 and 10. For example, the first matching layer 8 may be made of borosilicate glass and the second matching layer 10 may be made of acrylic resin plastic. The impedance matching layers transform the high acoustic impedance of the transducer elements to the low acoustic impedance of the human body and water.

The transducer package 2 further comprises a mass of suitable acoustical damping material positioned at the back surface of the transducer array 4. This backing layer 12 is coupled to the rear surface of the transducer elements 4 to absorb ultrasonic waves that emerge from the back side of each element so that they will not be partially reflected and interfere with the ultrasonic waves propagating in the forward direction.

The transducer elements, signal and ground connections, matching layers and backing layer are all bonded together to form the transducer package. During assembly of the ultrasonic probe, the transducer package must be held securely within the probe housing (not shown in FIG. 1). Typically, this is accomplished by securing the transducer package within a four-sided array case 14, i.e., a "box" having four side walls but no top or bottom walls. The array case is made of electrically conductive material and provides a common ground for connection with the ground electrodes of the transducer elements. During manufacture of the ultrasonic probe, the array case/transducer package combination is secured within the probe housing. The interior of the probe housing is then filled with thermal/acoustic potting material.

In most conventional probe designs, the array case and the outermost acoustic impedance matching layer 10 of the transducer package respectively form the four side walls and the bottom wall of a five-sided box when array case 4 and outermost matching layer 10 are bonded together, as shown in FIG. 2. Other portions of the transducer package 2 occupy the recess defined by the array case and the outermost matching layer 10. This construction has the disadvantage that the array case and the outermost matching layer must be separately fabricated and then the outermost matching must undergo two separate bonding operations: one when it is bonded to the transducer package and another when it is bonded to the array case. These multiple manufacturing steps increase the cost of manufacture.

SUMMARY OF THE INVENTION

The present invention is a monolithic transducer array case having a bottom wall which is suitable for use as an acoustic impedance matching layer in an ultrasonic transducer. The array case is made from electrically conductive material having an acoustic impedance less than the acoustic impedance of piezo-electric ceramic. The preferred material is copper-impregnated graphite. Copper-impregnated graphite is electrically conductive; is easy and inexpensive to precisely machine into the desired shape; has the desired acoustic impedance for use as a matching layer; and is very strong, yet lightweight. Thus, an array case which also performs the function of the outermost matching layer can be fabricated as a monolithic structure having the shape of a five-sided box.

In the alternative, the monolithic array case can be open at each end, i.e., a channel extends the full length of the array case. An open-ended monolithic array case is easier and cheaper to manufacture than is the closed-ended monolithic array case The advantages of using a monolithic array case over the conventional two-piece array case/matching layer combination include at least the following: (1) one machined piece is required instead of two independently machined pieces that must be bonded together later, thereby reducing the number of parts and the number of manufacturing steps; (2) the monolithic array case provides improved structural protection of the fragile transducer element array; and (3) a stronger ground connection is made between the array case and the adjacent transducer elements.

BRIEF DESCRIPTION OF THE DRAWINGS

FIGS. 3A, 3B and 3C are schematic front, top and end views, respectively, of a five-sided monolithic array case in accordance with one preferred embodiment of the invention.

DETAILED DESCRIPTION OF THE PREFERRED EMBODIMENTS

Figure 1:
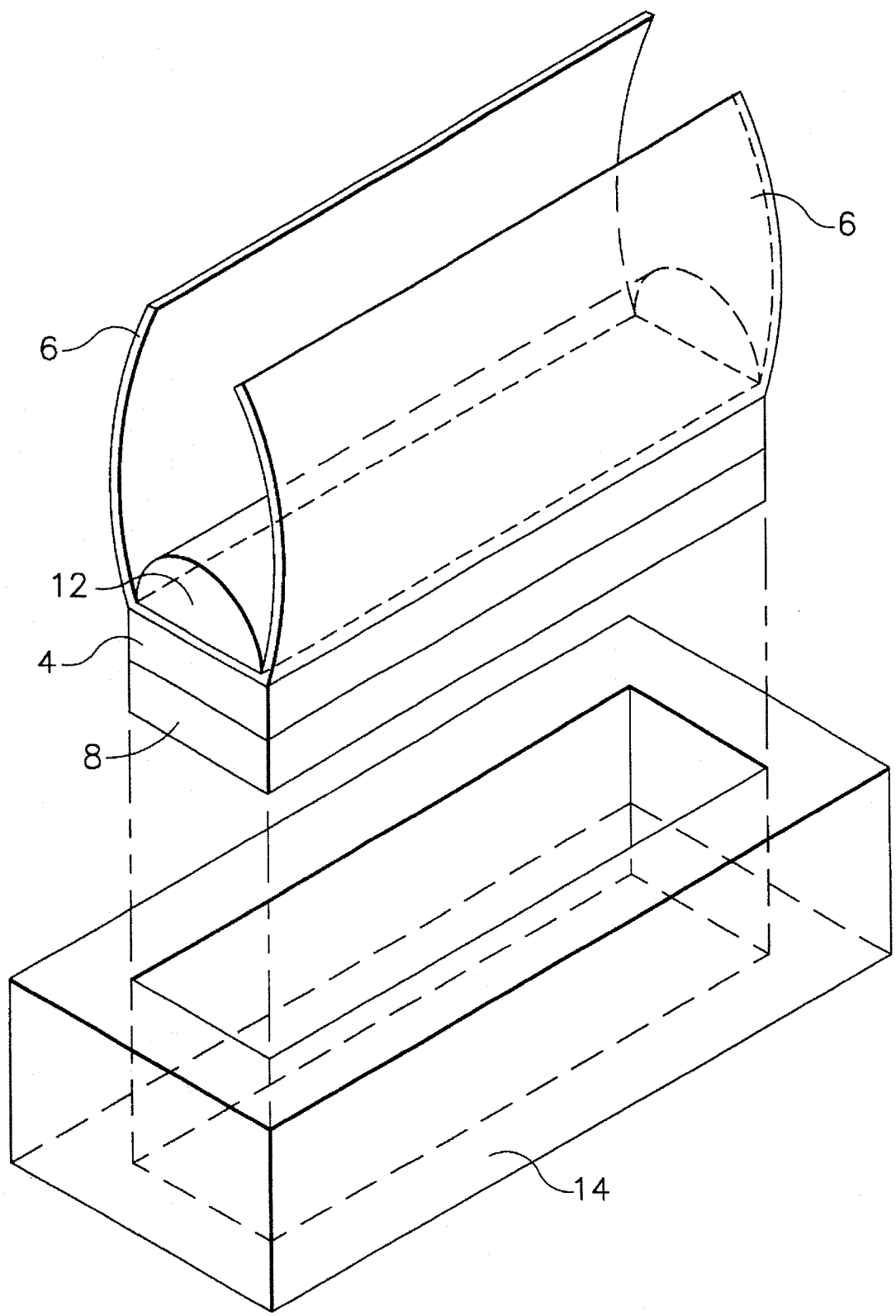
FIG. 1 is a schematic exploded view of the conventional stack-up of a transducer package and an array case for using an ultrasonic probe.
Figure 2:
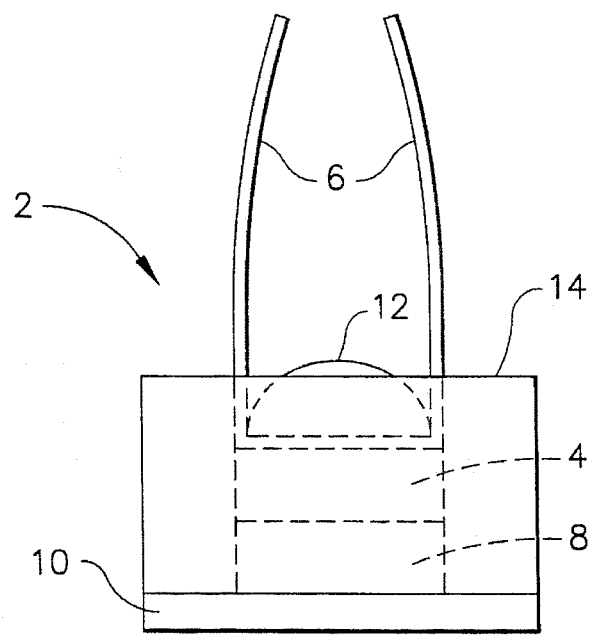
FIG. 2 is a schematic end view of the conventional transducer package/array case combination showing the five-sided box formed by the array case and the outermost matching layer.

Referring to FIGS. 3A, 3B and 3C, the monolithic array case 20 in accordance with one preferred embodiment of the invention comprises a five-sided box having right-angled corners. The array case has mutually parallel first and second side walls 22 and 24, mutually parallel first and second end walls 26 and 28 disposed perpendicular to side walls 22 and 24, and a bottom wall 30 disposed perpendicular to the side walls and end walls. Each of the first and second side walls 22 and 24 is integrally joined at opposing ends to the first and second end walls 26 and 28. The bottom wall 30 is integrally joined along its periphery to the bottom portions of the side walls and end walls.

Because the array case must function as a common ground to which the ground electrodes of the transducer array elements are connected, the array case must be made of electrically conductive material. In addition, because the bottom wall 30 of the array case must also serve as an acoustic impedance matching layer, the electrically conductive material must also have the desired acoustic impedance. A preferred electrically conductive material is copper-impregnated graphite. Copper-impregnated graphite is easy and inexpensive to precisely machine into the desired shape. It is also very strong, yet lightweight. Other suitable materials having similar properties may be used instead of copper-impregnated graphite.

The five-sided monolithic array case is formed from a solid block of material by ultrasonic machining. In accordance with this technique, a tool in the shape of the desired recess 32 is coupled to an ultrasonic horn (not shown). Preferably, recess 32 has a rectangular cross section. A slurry of abrasive particles is placed between the tool and the horn. When the tool is vibrated by the ultrasonic horn, the abrasive particles abrade the material of the block. This process is continued until the final desired shape of the recess 32 is obtained. Thereafter, a further recess 34 is formed in the upper surface of the bottom wall 30 by ultrasonic machining. In this ultrasonic machining step, a tool is used having a smaller cross section than the tool used in the first ultrasonic machining step. Preferably, recess 34 has a rectangular cross section. The width and length of recess 34 are selected to match the width and length of the bottom of the transducer package, which is inserted therein. Recess 32 has a width and a length respectively greater than the width and length of recess 34 in order to provide a gap between the walls of the array case and the sides of the transducer package. This gap is filled with bonding adhesive, e.g., a thermosetting epoxy resin. The recess 34 serves to center the transducer package 2 relative to the array case while the epoxy resin is setting.

Figure 4:
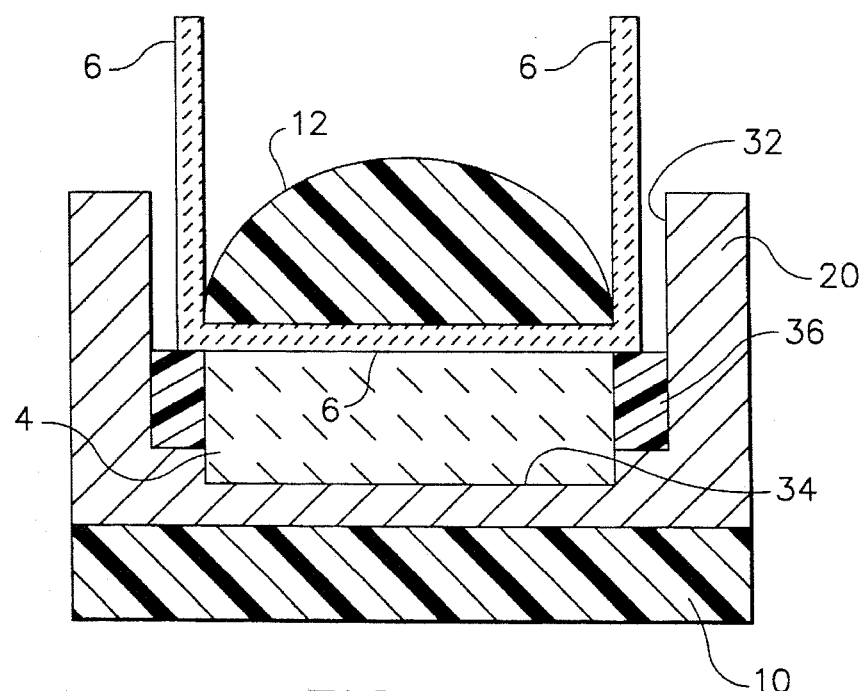
FIG. 4 is a schematic isometric view of a three-sided open-ended monolithic array case in accordance with another preferred embodiment of the invention.
Figure 5:
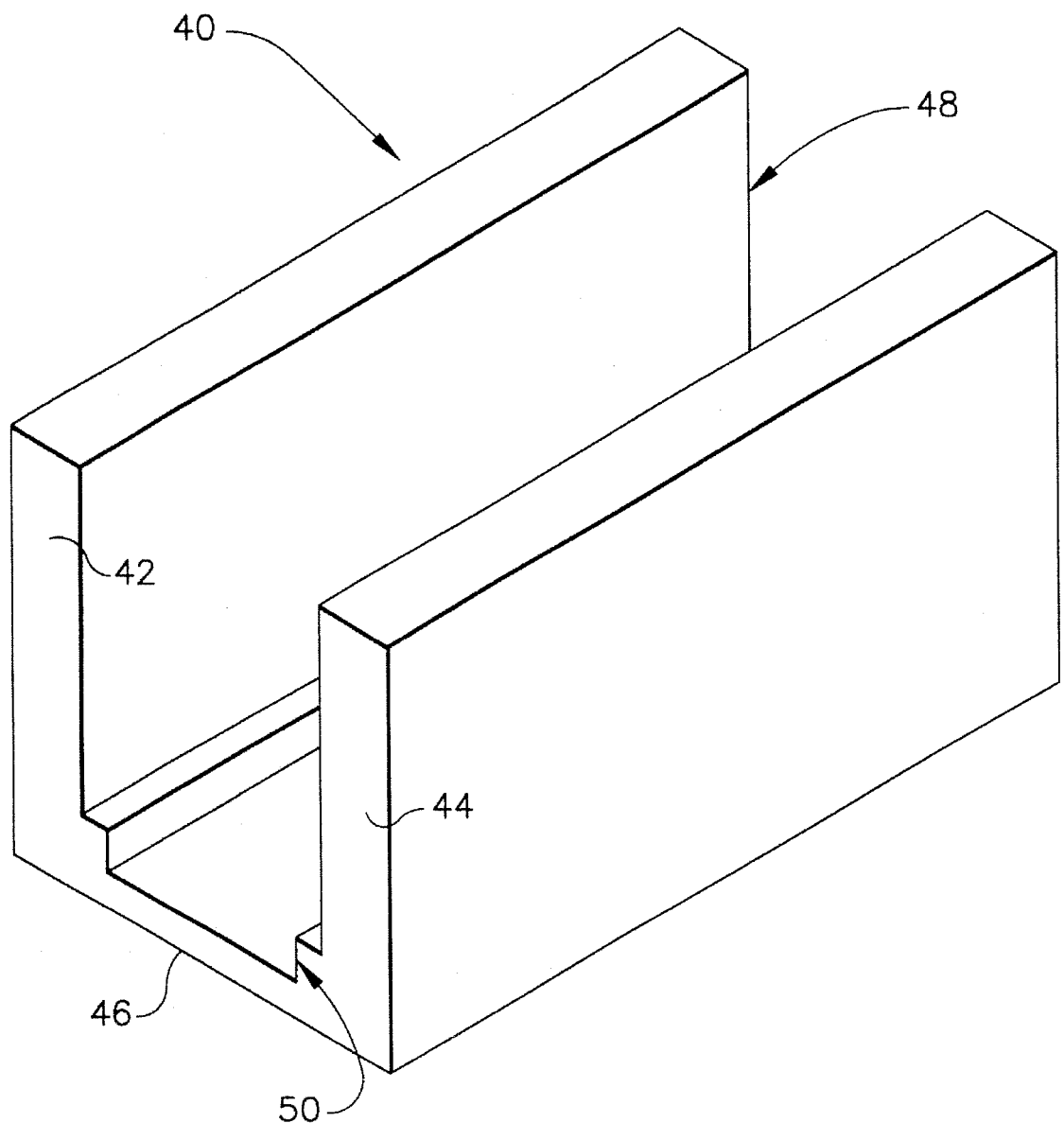
FIG. 5 shows three-sided, open-ended array case.

In accordance with another preferred embodiment of the invention, the array case is formed as a three-sided open-ended structure 40, as seen in FIG. 4. Starting with the same solid block of material used to make the five-sided box, the three-sided structure consisting of a pair of side walls 42 and 44 and a bottom wall 46 can be fabricated by milling or grinding a first channel 48 of constant cross section from one end of the block to the other end. The width of the channel 48 should be slightly greater than the width of the transducer package. In a second milling or grinding step, a second channel 50 can be formed on the bottom wall 46 in communication with channel 48. Channel 50 serves the same purpose as recess 34 in FIG. 3A, namely, to center the transducer package 2 relative to the array case while the epoxy resin in the gaps between array case walls 42 and 44 and the transducer package is setting.

The foregoing preferred embodiments have been disclosed for the purpose of illustration. Variations and modifications which do not depart from the broad concept of the invention will be readily apparent to those skilled in the design of ultrasonic probes. All such variations and modifications are intended to be encompassed by the claims set forth hereinafter.

We claim:
1. An ultrasonic transducer comprising:
   a transducer package comprising a plurality of transducer elements made of piezoelectric ceramic and a backing layer made of acoustic damping material, each of said transducer elements having a back surface coupled to said backing layer and having a front surface; and
   a monolithic transducer array case comprising a bottom wall having first and second side portions, a first side wall having a top portion and a bottom portion, and a second side wall having a top portion and a bottom portion, wherein said bottom portion of said first side wall is integrally formed with said first side portion of said bottom wall and said bottom portion of said second side wall is integrally formed with said second side portion of said bottom wall, and said first and second side walls and said bottom wall are made of a non-metal impregnated with a metal, said integrally formed bottom and first and second side walls having a U-shaped cross section defining an internal space, wherein said transducer package is located in said internal space of said monolithic transducer array case in contact with said bottom wall.

2. The ultrasonic transducer as defined in claim 1, wherein said non-metal is graphite.

3. The ultrasonic transducer as defined in claim 1, wherein said non-metal is graphite and said metal is copper.

4. The ultrasonic transducer as defined in claim 1, wherein said bottom wall has first and second end portions, said first side wall has first and second end portions and said second side wall has first and second end portions, further comprising a first end wall having first and second side portions and a bottom portion, and a second end wall having first and second side portions and a bottom portion, wherein said first and second side portions and said bottom portion of said first end wall are integrally formed with said first end portions of said first side wall, said second side wall and said bottom wall respectively, and said first and second side portions and said bottom portion of said second end wall are integrally formed with said second end portions of said first side wall, said second side wall and said bottom wall respectively, whereby a five-sided box with an open top is formed.

5. The ultrasonic transducer as defined in claim 4, wherein said first and second end walls are made of the same material which said bottom wall and said first and second side walls are made of.

6. The ultrasonic transducer as defined in claim 1, wherein said bottom wall of said monolithic transducer array case serves as a first acoustic impedance matching layer, and said transducer package further comprises a second acoustic impedance matching layer which is acoustically coupled to said first acoustic impedance matching layer of said monolithic transducer array case.

7. The ultrasonic transducer as defined in claim 1, wherein said metal-impregnated non-metal has an acoustic impedance less than the acoustic impedance of aluminum.

* * * * *